United States Patent [19]

Chapdelaine et al.

[11] Patent Number: 5,254,683
[45] Date of Patent: Oct. 19, 1993

[54] THERAPEUTIC BENZAZARINE COMPOUNDS

[75] Inventors: Marc J. Chapdelaine, Wilmington, Del.; Charles D. McLaren, Landenberg, Pa.

[73] Assignee: Imperial Chemical Industries PLC, London, England

[21] Appl. No.: 816,327

[22] Filed: Dec. 31, 1991

[30] Foreign Application Priority Data

Jan. 2, 1991 [GB] United Kingdom ............... 9100028

[51] Int. Cl.$^5$ .................... C07D 223/16; A61K 31/55
[52] U.S. Cl. .................................. 540/523; 514/213
[58] Field of Search ........................................ 540/523

[56] References Cited

U.S. PATENT DOCUMENTS

| | | | |
|---|---|---|---|
| 4,410,520 | 10/1983 | Watthey | 424/244 |
| 4,473,575 | 9/1984 | Watthey | 424/263 |
| 4,575,503 | 3/1986 | Watthey | 514/213 |

FOREIGN PATENT DOCUMENTS

| | | | |
|---|---|---|---|
| 0072352 | 2/1983 | European Pat. Off. | 540/523 |
| 0130538 | 1/1985 | European Pat. Off. | 540/523 |
| 3416695 | 11/1985 | Fed. Rep. of Germany | |
| 1340334 | 12/1973 | United Kingdom | 540/523 |
| 2103614 | 2/1983 | United Kingdom | 540/523 |
| WO9105549 | 5/1991 | World Int. Prop. O. | 540/523 |

OTHER PUBLICATIONS

Swartz et al, Molecular Pharmacology, 41:1130–1141 (1992).
Can. J. Chem. 52, 610, (1974).
J. Heterocyclic Chem., 26, 793, (1909).
Abstract of EP-166-353-A, no date given.
Abstract of EP-166-357-A, no date given.
Abstract of EP-166-354-A, no date given.
Abstract of U.S. Pat. No. 4,692,522, no date given.
Abstract of U.S. Pat. No. 4,757,068, no date given.
Abstract of EP-322-779-A, no date given.
Abstract of ZA 8303-903-A, no date given.
Abstract of EP-107-095-A, no date given.
Abstract of ZA 8309-532-A, no date given.
Abstract of U.S. Pat. No. 3,989,689, no date given.
Abstract of Jap. 4028-754, no date given.
Abstract of U.S. Pat. No. 4,477,446, no date given.
Abstract of U.S. Pat. No. 3,949,081, no date given.
Abstract of U.S. Pat No. 4,965,356, no date given.
Abstract of EP 400–665-A, no date given.

Primary Examiner—Robert T. Bond
Attorney, Agent, or Firm—Cushman, Darby & Cushman

[57] ABSTRACT

A method for the treatment of neurological disorders, comprising administering to a mammal in need of such treatment an effective amount of a compound of formula I or of formula II (formulae set out on pages following the Examples), wherein
$R^1$, $R^2$, $R^3$ and $R^4$ are independently selected from:
hydrogen,
(1–3C)perfluoroalkyl,
halo, nitro and cyano;
$R^5$ is a (1–5C)alkyl group;
or a pharmaceutically acceptable salt thereof.

Also provided are compounds and pharmaceutical compositions suitable for the treatment of neurological disorders.

7 Claims, No Drawings

THERAPEUTIC BENZAZARINE COMPOUNDS

This invention relates to benz[b]azepine compounds useful in the treatment of neurological disorders generally in mammals such as man. More specifically, the compounds are useful in the treatment of strokes and/or other neurodegenerative disorders such as hypoglycemia, cerebral palsy, transient cerebral ischemic attack, perinatal asphyxia, epilepsy, psychosis, Huntington's chorea, amyotrophic lateral sclerosis, Alzheimer's disease, Parkinson's disease, Olivo-pontocerebellar atrophy, viral-induced neurodegeneration such as in acquired immunodeficiency syndrome and its associated dementia, anoxia such as from drowning, spinal cord and brain trauma, poisoning by exogenous neurotoxins, and chronic pain, for the prevention of drug and alcohol withdrawal symptoms, and for the inhibition of tolerance and dependence to opiate analgesics. The invention particularly relates to novel benz[b]azepine compounds useful in reducing neurological degeneration such as can be induced by a stroke and the associated functional impairment which can result. Treatment using a compound of the invention can be remedial or therapeutic as by administering a compound following an ischemic event to mitigate the effects of that event. Treatment can also be prophylactic or prospective by administering a compound in anticipation that an ischemic event may occur, for example in a patient who is prone to stroke.

It is known that ischemic events can trigger a dramatic increase in extracellular concentrations of the excitatory amino acids glutamate and aspartate which can, in turn, cause prolonged neuronal excitation leading to a massive influx of calcium from extracellular to intracellular sites in brain neural cells. A calcium overload can thereby be created which leads to a cascade of events leading to cell catabolism and eventually resulting in cell death. The N-methyl-D-aspartate (NMDA) receptor complex is believed to play a significant role in the cascade of events leading to cell necrosis following an ischemic event.

The compounds provided by this invention may be useful in a variety of neurodegenerative disorders because they function as excitatory amino acid antagonists. They may do so indirectly, via allosteric modulation of the glutamate binding site, specifically by acting as antagonists of the strychnine-insensitive glycine receptor on the NMDA receptor complex. They may also do so directly, by binding to the glutamate site itself on the NMDA receptor complex.

According to the invention there is provided a method for the treatment of neurological disorders, comprising administering to a mammal in need of such treatment an effective amount of a compound of formula I or of formula II (formulae set out, together with other formulae referred to by Roman Numerals, on pages following the Examples), wherein $R^1$, $R^2$, $R^3$ and $R^4$ are independently selected from:
hydrogen,
(1-3C)perfluoroalkyl,
halo, nitro and cyano;
$R^5$ is a (1-5C)alkyl group;
or a pharmaceutically acceptable salt thereof.

Thus the present invention also provides a compound of formula I or of formula II (as defined above), or a pharmaceutically acceptable salt thereof, for use in medicine; and in particular for use in the treatment of neurological disorders.

The invention further provides pharmaceutical compositions for the treatment of neurological disorders comprising a compound of formula I or of formula II as defined above, or a pharmaceutically acceptable salt thereof, and a pharmaceutically acceptable diluent or carrier.

Certain compounds having formula I are known from UK Patent Specification 1 340 334, and also from Birchall and Rees, Can. J. Chem., 52, 610 (1974). However, novel compounds of this invention include those of formula I and formula II wherein $R^2$ and $R^3$ are not both (independently) selected from the group consisting of hydrogen and halogen when $R^1$ and $R^4$ are hydrogen.

While not wishing to be bound by theory, it is believed that compounds of formula II may be converted to the 3-hydroxy derivatives in vivo, and that they may accordingly be acting as prodrugs.

In this specification the term "alkyl" includes both straight and branched chain radicals, but it is to be understood that references to individual radicals such as "propyl" embrace only the straight chain ("normal") radical, branched chain isomers such as "isopropyl" being referred to specifically.

"Halo" as used generally herein means fluoro, chloro, bromo, or iodo.

It will be appreciated by those skilled in the art that many of the compounds disclosed herein can exist and be drawn in various tautomeric forms, and all references to any particular structure are understood to include the various tautomeric forms thereof.

Particular values of (1-5C)alkyl include methyl, ethyl, propyl, isopropyl, butyl, isobutyl, pentyl, isopentyl, and neopentyl.

Particular values of $R^1$-$R^4$ as (1-3C)perfluoroalkyl include trifluoromethyl, pentafluoroethyl, and heptafluoropropyl.

Particular values of $R^1$-$R^4$ as halo include fluoro, chloro, bromo, and iodo.

More particular values of (1-5C)alkyl include methyl, ethyl, and propyl.

More particular values of $R^1$-$R^4$ as (1-3C)perfluoroalkyl include trifluoromethyl and pentafluoroethyl.

More particular values of $R^1$-$R^4$ as halo include fluoro, chloro, and bromo.

Preferred values of $R^1$, $R^2$, $R^3$, and $R^4$ include hydrogen and halo.

Preferred values of (1-5C)alkyl include methyl and ethyl.

More preferred values of $R^1$ and $R^3$ include hydrogen, fluoro, chloro, and bromo.

More preferred values of $R^2$ and $R^4$ include hydrogen.

Preferred compounds of the invention include:
8-chloro-2,5-dihydro-2,5-dioxo-3-hydroxy-1H-benz[b]azepine;
7-chloro-2,5-dihydro-2,5-dioxo-3-hydroxy-1H-benz[b]azepine;
8-bromo-2,5-dihydro-2,5-dioxo-3-hydroxy-1H-benz[b]azepine;
8-fluoro-2,5-dihydro-2,5-dioxo-3-hydroxy-1H-benz[b]azepine;
6,8-dichloro-2,5-dihydro-2,5-dioxo-3-hydroxy-1H-benz[b]-azepine;
6,8-dibromo-2,5-dihydro-2,5-dioxo-3-hydroxy-1H-benz[b]-azepine;

6,8-difluoro-2,5-dihydro-2,5-dioxo-3-hydroxy-1H-benz[b]-azepine;

and the (1–5C)alkyl enol ethers thereof (i.e., compounds of formula II where $R^5$ is (1–5C)alkyl), especially the methyl and ethyl enol ethers.

Benz[b]azepines of formula I can be made by processes which include processes known in the chemical arts for the production of structurally analogous compounds. Such processes for the manufacture of a benz[b]azepine of formula I as defined above are provided as further features of the invention and are illustrated by the following procedures in which the meanings of generic radicals are as given above unless otherwise qualified. Such a process can be effected, generally, by reacting a compound of formula II, wherein $R^5$ is a (1–5C)alkyl group, such as methyl or ethyl, with a boron trihalide.

If not commercially available, the necessary starting materials for the procedures such as that described above may be made by procedures which are selected from standard organic chemical techniques, techniques which are analogous to the synthesis of known, structurally similar compounds, or techniques which are analogous to the above described procedure or the procedures described in the examples.

A compound of formula II can be made by reacting a corresponding alkyl enol ether of formula III with sodium azide in neat trifluoromethanesulfonic acid or concentrated sulfuric acid (Schmidt reaction) at a temperature of about 0° C. to about room temperature. Trifluoromethanesulfonic acid is preferred in cases where any one or more of $R^1$–$R^4$ is halogen. $R^5$ is preferably methyl or ethyl to facilitate the Schmidt reaction.

A methyl enol ether of formula III can be made by reacting a corresponding hydroxy naphthoquinone of formula IV with a corresponding alcohol having the formula $R^5OH$, such as methanol or ethanol, in the presence of a suitable acid such as anhydrous hydrogen chloride. Hydroxy naphthoquinones of formula IV can be made by oxidizing a corresponding tetralone of formula V or of formula Va. The oxidation can be effected conveniently as a one-pot process in a suitable solvent such as tert-butanol and in the presence of a suitable base such as potassium tert-butoxide, with oxygen bubbled through the rection mixture. It will also be appreciated by those skilled in the art that suitable stepwise or multi-pot variations of the one-pot process can be implemented.

Many tetralones of formula V and/or Va suitable for use in the invention are either available commercially or can be made by procedures already known in the art. For example, a 1-tetralone of formula V can be made by cyclizing a corresponding acid of formula VI under acidic conditions, for example with polyphosphoric acid with the application of heat. A 2-tetralone of formula Va can be made by ethylene insertion into the corresponding phenylacetic acid chloride of formula VIa, followed by cyclization, following the general method of Rosovsky et al, *J. Org. Chem.*, 33, 4288 (1968).

Compounds of formula VI can be made by reducing a corresponding ketone, for example, by reducing a compound of formula VII by methods known to the art, e.g. a Volff-Kishner reduction for the reduction of carbonyl groups using hydrazine and base.

Compounds of formula VIa can be made by converting a benzylic alcohol of formula VIII (X=OH) to a corresponding benzylic chloride (X=Cl) (e.g., by reacting with an appropriate reactant such as thionyl chloride), followed by reacting the benzyl chloride thus formed with a suitable alkali metal cyanide (e.g., sodium cyanide) to effect cyanide displacement of chloride and thereby form a corresponding benzylic cyanide (X=CN). An acid of formula VIa can be prepared as known in the art by hydrolyzing the benzylic cyanide under acidic conditions.

Alternatively, acids of formula VIa can be formed by brominating a toluene corresponding to formula VIII wherein X=H to form the corresponding benzylic bromide (X=Br), followed by displacement with cyanide as described above to form acid VIa.

It is noted that many enol ethers of formula III can also be made along the lines generally disclosed in S. T. Perri et. al., *Org. Syn.*, 69, 220 and in J. M. Heerding and H. W. Moore, *J. Org. Chem.*, 56, 4048–4050, (1991). The synthesis is generally illustrated in Scheme I (set forth on pages following the Examples) as follows. Organolithium compound 10 can be reacted with semisquarate or semisquaric acid compound 12 to thereby produce 4-(disubstitutedaryl)-3-alkoxy-4-hydroxy-2-cyclobutenone 14. It is noted that semisquarate compound 12 can be readily obtained, as set forth in Heerding and Moore, supra, by treatment of a dialkyl squarate (such as diethyl, diisopropyl, or dibutyl squarate, all available commercially from Aldrich) with a suitable reducing agent such as lithium tri-tert-butoxyaluminohydride, followed by hydrolysis of the intermediate 13 thereby obtained in aqueous hydrochloric acid. Compound 14 can in turn be converted, by heating in a suitable solvent such as xylene, to the hydroquinone 16. Hydroquinone 16 can then be oxidized (e.g. with ferric chloride) to the corresponding naphthoquinone 18. If necessary preparatory to conducting the Schmidt reaction on the naphthoquinone, naphthoquinone 18 can be transetherified, for example with methanolic hydrochloric acid, thereby yielding the methoxy naphthoquinone 20 having formula III.

Examples of suitable pharmaceutically acceptable salts are salts formed with bases which form a physiologically acceptable cation, such as alkali metal (for example, sodium and potassium), alkaline earth metal, aluminum and ammonium salts, as well as salts made with appropriate organic bases such as triethylamine, morpholine, piperidine, and triethanolamine. Care should be taken to avoid metals and/or metal compositions which may result in a metal catalyzed decomposition of the active ingredient.

When used to intervene therapeutically following a stroke, a benz[b]azepine of formula I generally is administered as an appropriate pharmaceutical composition which comprises a benz[b]azepine of formula I as defined hereinbefore together with a pharmaceutically acceptable diluent or carrier, the composition being adapted for the particular route of administration chosen. Such compositions are provided as a further feature of the invention. They may be obtained employing conventional procedures and excipients and binders and may be in a variety of dosage forms. For example, they may be in the form of tablets, capsules, solutions or suspensions for oral administration; in the form of suppositories for rectal administration; and in the form of sterile solutions or suspensions for administration by intravenous or intramuscular injection or infusion.

The dose of compound of formula I which is administered will necessarily be varied according to principles well known in the art taking account of the route of administration, the severity of the ischemic disorder, and the size and age of the patient. In general, a compound of formula I will be administered to a warm blooded animal (such as man) so that an effective dose is received, for example a dose in the range of about 0.1 to about 10 mg/kg intravenous body weight.

It will be apparent to those skilled in the art that a compound of formula I can be co-administered with other therapeutic or prophylactic agents and/or medicaments that are not medically incompatible therewith.

The actions of compounds of formula I as antagonists at the glycine receptor of the NMDA receptor complex can be shown by standard tests such as the [$^3$H]-glycine binding assay, by functional assays in vitro such as tests for measuring glutamate evoked contractions of the guinea pig ileum, and by tests in vivo such as ischemia induced by carotid occlusion in the gerbil model.

In the [$^3$H]-glycine binding assay, neuronal synaptic membranes are prepared from adult (about 250 g) male Sprague-Davley rats. Freshly dissected cortices and hippocampi are homogenized in 0.32M sucrose (110 mg/mL). Synaptosomes are isolated by centrifuga-tion (1000 xg, 10 min), the supernatant is pelleted (20,000 xg, 20 min) and resuspended in double-distilled water. The suspension was centrifuged for 20 minutes at 8,000 xg. The resulting supernatant and buffy coat are washed twice (48,000 xg, 10 mins, resuspension in double-deionized water). The final pellet is quickly frozen (dry ice/ethanol bath) under double-deionized water and stored at $-70°$ C.

On the day of the experiment, thawed synaptic membranes are homogenized with a Brinkmann Polytron (tm, Brinkmann Instruments, Westbury, N.Y.) tissue homogenizer in 50 mM tris(hydroxymethyl)-aminomethane citrate, pH 7.1. The membranes are incubated with 0. 04% Sufact-AMPS X100 (tm, Pierce, Rockford, Ill.) in buffer for 20 minutes at 37° C. and washed six times by centrifugation (48,000 xg, 10 min) and resuspended in buffer. The final pellet is homogenized at 200 mg wet weight/ml of the buffer for the binding assay.

For [$^3$H]-glycine binding at the N-methyl-D-aspartate receptor, 20 nM [$^3$H]-glycine (40-60 Ci/mmol, New England Nuclear, Boston, Mass.) is incubated with the membranes suspended in 50 mM tris (hydroxymethyl)aminomethane citrate, pH 7.1 for 30 minutes at 4° C. Glycine, 1 mM, is used to define the nonspecific binding. Bound [$^3$H]-glycine is isolated from free using a Brandel (Biomedical Research and Development Laboratories, Gaithersburg, Md.) cell harvester for vacuum filtration over glass fiber filters (Whatman GF/B from Brandel, Gaithersburg, Md.) presoaked in 0.025% polyethylenimine. The samples retained on the glass fiber filters are rinsed 3 times with a total of 2.5 mL ice cold buffer. Radioactivity is estimated by liquid scintillation counting. $IC_{50}$ values are obtained from a least-squares regression of a logit-log transformation of the data. Typical $IC_{50}$ values for compounds of the invention are illustrated by the compound of Example 1 ($IC_{50}=30$ nanomolar (nM)), Example 3 ($IC_{50}=97$ nM), and Example 1a ($IC_{50}=1.0$ micromolar ($\mu$M).

For glutamate evoked contractions of the guinea pig ileum, the methodology is as described previously (Luzzi et. al., *Br. J. Pharmacol.*, 95, 1271-1277 (1989). The longitudinal muscle and associated myenteric plexus are removed and placed in oxygenated modified Krebs-Henseleit solution (118 mM NaCl, 4.7 mM KCl, 2.5 mM $CaCl_2$, 1.2 mM $KH_2PO_4$, 25 mM $NAHCO_3$, and 11 mM glucose). Tissues are suspended on glass rods in organ baths under a resting tension of 0.5 g. After an initial depolarization with 80 mM potassium to remove possible blockade of the NMDA receptor channel complex with magnesium, witch responses are evoked with 100 $\mu$M glutamate. Isometric mechanical responses are recorded. Tissues are equilibrated for at least 2 hours prior to addition of compounds.

A dose response curve for the effect of the unknown on the magnitude of the glutamate-evoked contractions is generated. Glutamate-evoked contractions are generated at 20 minute intervals, with the test compound added 5 minutes before the glutamate. The magnitude of the contraction with each dose of the unknown is expressed relative to the control, the third contraction evoked by 100 $\mu$M glutamate alone in the same tissue bath. The $IC_{50}$ is obtained from a least-squares regression of a logit-log transformation of the data. Typical $IC_{50}$ values for compounds according to the invention are illustrated by the compound of Example 1 ($IC_{50}=0.11$ $\mu$M) and Example 3 ($IC_{50}=1.0$ $\mu$M).

After the last contraction for the dose-response curve, 100 $\mu$M glycine is added to the bath 10 minutes after the previous addition of glutamate. 10 minutes later the estimated $IC_{50}$ to $IC_{70}$ dose of the test compound is added and 10 minutes later glutamate is used to evoke the contraction. The "glycine reversal" is the ability of glycine to compete with the unknown and to prevent the inhibition previously seen by the dose of the unknown.

When testing in vivo using the gerbil ischemic model, adult female Mongolian gerbils (50-70 g) are anesthetized with 2 to 3% halothane. The bilateral common carotid arteries at the neck are exposed and occluded with microaneurysm clips. After 10 min (unless specified), the clips are removed and the blood flow through the carotid arteries is restored and the skin is sutured. Test compounds are administered intraperitoneally both pre- and post-occlusion, for example 45 minutes before and 5 minutes after occlusion of the carotid arteries. Sham-operated animals are treated in the same manner except that the arteries are not clamped. Gross behavioral observations along with motor activity are recorded for 2 hr on the first (24 hr) day following the occlusion. After 4 days, subjects are sacrificed (decapitation), brains are removed, fixed, sectioned and stained with hematoxylin/eosin and cresyl violet.

The brain sections are rated for neuronal damage in the hippocampus using the following rating scale:
0=undamaged, normal
1=slight damage (up to 25%)—restricted CA1/-subiculum border
2=moderate damage (up to 50%)—obvious damage, restricted to less than half of CA1 field
3=marked damage (up to 75%)—involving greater than half of CA1 field
4=damage extending beyond CA1 field
Results can be reported as the percentage of neuroprotection afforded by a particular dose and dosing regimen.

Sections (7 micron) are evaluated from each brain. Occasionally, asymmetrical damage may be noted and the rating assigned is the average score of the two sides. The average brain damage rating score for each group is recorded, and the damage scores of the drug treated group are compared to the vehicle-treated group using Wilcoxcon-Rank Sum test.

Typical values in this test for compounds according to the invention are illustrated by the following results: for the compound of Example 1, 57% neuroprotection (relative to sham-operated control) when dosed twice with 20 mg/kg body weight intraperitoneally (ip) according to the above regimen; 44% neuroprotection when dosed with 30 mg/kg body weight ip three times at 15, 30, and 45 minutes after induction of ischemia; for the compound of Example 3, 83% neuroprotection when dosed twice with 30 mg/kg body weight ip according to the above regimen; for the compound of Example 1a, 78% neuroprotection when dosed twice with 20 mg/kg body weight ip according to the above regimen.

The invention will now be illustrated by the following non-limiting examples in which, unless stated otherwise:

(i) temperatures are given in degrees Celsius (°C.); operations were carried out at room or ambient temperature, that is, at a temperature in the range of 18°-25° C.;

(ii) evaporation of solvent was carried out using a rotary evaporator under reduced pressure (600-4000 pascals; 4.5-30 mm Hg) with a bath temperature of up to 60° C.;

(iii) flash chromatography was carried out on 40 μM silica gel flash chromatography packing obtained from J. T. Baker; thin layer chromatography (TLC) was carried out on Analtech 0.25 mm silica gel GHLF plates (Art 21521), obtainable from Analtech, Newark, Del., USA;

(iv) in general, the course of reactions was followed by TLC and reaction times are given for illustration only;

(v) melting points are uncorrected and (dec) indicates decomposition; the melting points given are those obtained for the materials prepared as described; polymorphism may result in isolation of materials with different melting points in some preparations;

(vi) all final products were essentially pure by TLC and had satisfactory nuclear magnetic resonance (NMR) spectra and microanalytical data;

(vii) yields are given for illustration only;

(viii) reduced pressures are given as absolute pressures in Pascals (Pa); other pressures are given as gauge pressures in bars;

(ix) chemical symbols have their usual meanings; the following abbreviations have also been used: v (Volume), v (weight); mp (melting point), L [liter(s)], mL (milliliters), mM (millimoles), g [gram(s)], mg [milligram(s)];

(x) solvent ratios are given in volume: volume (v/v) terms, unless indicated otherwise; and (xi) conventional acronyms have been employed such as NMR (nuclear magnetic resonance), THF (tetrahydrofuran), DMSO (dimethylsulfoxide), DMF (dimethylformamide), TFA (trifluoroacetic acid), and so forth.

EXAMPLE 1

8-Chloro-2,5-dihydro-2,5-dioxo-3-hydroxy-1H-benz[b]azepine [Formula I: $R^1=R^2=R^4H$; $R^3=Cl$]

8-Chloro-2,5 -dioxo-3-methoxy-1H-benz[b]azepine [Formula II: $R^1=R^2=R^4H$; $R^3=Cl$; $R5=CH_3$] (0.0789 g, 0.332 mM) was added to a solution of 1.01 mL (1.0M, $CH_2Cl_2$) boron tribromide in 1.8 mL dry methylene chloride under nitrogen. The suspension was stirred at room temperature for 0.42 hours. The reaction mixture was poured into 7 mL of saturated aqueous sodium bicarbonate and stirred for 0.25 hours. The homogeneous solution was then adjusted to pH=5 by slow addition of concentrated hydrochloric acid. The precipitate was vacuum filtered and washed with water to give 0.0683 g (92%) of white solid which was recrystallized from 5 mL DMF and 1 mL of water. After cooling in an ice bath, solid was collected by vacuum filtration, washed with water and vacuum dried at 100° C. and 15 Pa to give 0.056 g (75%) of product; mp 308.5–310.5 (dec); NMR (DMSO-$d_6$, 300 MHz): 11.57 (s,1H, N—H), 10.86 (brs,1H, O—H), 8.04 (d,1H, $J_{ortho}=8.7$ Hz), 7.54 (d,1H, $J_{meta}=2.0$ Hz), 7.31 (dd,1H, $J_{ortho}=8.7$, $J_{meta}=2.0$ Hz), 6.41 (s,1H); Analysis for $C_{10}H_6ClNO_3$ Calculated: C, 53.71; H, 2.70; N, 6.26.

Found: C, 53.30; H, 2.74; N, 6.29.

Examples 1a–1e describe and disclose a sequential synthetic route for making the intermediate used to make the title compound of Example 1.

EXAMPLE 1a (PROCEDURE A)

8-Chloro-2,5-dihydro-2,5-dioxo-3-methoxy-1H-benz[b]azepine [Formula II: $R^1=R^2=R^4=H$; $R^3=Cl$; $R^5=CH_3$]

7-Chloro-2-methoxy-1,4-napthoquinone [Formula III: $R^1=R^2=R^4=H$; $R^3=Cl$; $R^5=CH_3$] (0.71 g, 3.2 mill) was added to 4.1 mL of concentrated sulfuric acid chilled in an ice bath. The cold red solution was stirred under nitrogen and sodium azide added (0.23 g. 3.5 mM). The reaction mixture was maintained in an ice bath for 0.33 hours then allowed to warm to room temperature and maintained thus for 18 hours. The reaction mixture was recooled in an ice bath and an additional portion of sodium azide added (0.21 g, 3.2 mM). After 0.33 hours the mixture was allowed to warm to room temperature for 20 hours. Once again the mixture was cooled in an ice bath and sodium azide added (0.21 g, 3.2 mM); the mixture was maintained in an ice bath for 0.33 hours and then room temperature for 68 hours. The reaction mixture was then poured into 200 mL of ice cold saturated aqueous sodium bicarbonate. The resulting precipitate was filtered off, washed with water to give after vacuum drying (25° C., 15 Pa) 0.343 g (45%) of dark solid. The solid was recystallized from 3 mL DMF and 1 mL of water to give 0.2 g (26%) of white solid; NMR(DMSO-$d_6$, 250 MHz): 11.39(s,1H, N—H), 7.93(d,1H, $J_{ortho}=8.8$ Hz), 7.47(d,1H, $J_{meta}=1.7$ Hz), 7.28(dd,1H, $J_{ortho}=8.8$ Hz, $J_{meta}=1.7$ Hz) 6.35(s,1H), 3.80(s,3H).

EXAMPLE 1a (PROCEDURE B)

8-Chloro-2,5-dihydro-2,5-dioxo-3-methoxy-1H-benz[b]azepine [Formula II; $R^1=R^2=R^4=H$; $R^3=Cl$; $R^5=CH_3$]

7-Chloro-2-methoxy-1,4-naphthoquinone [Formula III: $R^1=R^2=R^4=H$; $R^3=Cl$; $R^5=CH_3$] (14.74 g, 66.2 mM) was added to trifluoromethanesulfonic acid (153 ml) chilled in an ice bath under nitrogen. The solution was stirred under nitrogen and sodium azide added (4.74 g, 73.0 mM). The reaction mixture was maintained in an ice bath for 0.33 hours then allowed to warm to room temperature and maintained thus for 90 hours. The reaction mixture was recooled in an ice bath and an additional portion of sodium ozide added (2.15 g, 33.1 mM). After 0.08 hours the mixture was allowed to warm to room temperature for 19 hours. The reaction mixture was then poured into ice cold aqueous sodium bicarbonate (153 g, 1.82M in 2.3L). The resulting precipitate was filtered off, washed with water to give after vacuum drying (25° C., 15 Pa) 13.83 g of tan solid. The solid was recrystallized from 300 mL of hot DMF. After cooling in an ice bath, the solid was filtered off, washed with cold DMF followed by water to give after vacuum drying (25° C., 15Pa) 8.12 (52%) of light tan solid; mp 340–342 (dec).

Analysis for $C_{11}H_8ClNO_3$:
Calculated: C, 55.60; H, 3.39; N, 5.89. Found: C, 55.35; H, 3.38; N, 6.07.

EXAMPLE 1b

7-Chloro-2-methoxy-1,4-naphthoquinone [Formula III: $R^1=R^2=R^4=H; R^3=Cl; R^5=CH_3$]

7-Chloro-2-hydroxy-1,4-naphthoquinone [Formula III: $R^1=R^2=R^4=R^5=H; R^3=Cl$] (0.73 g, 3.5 mM) was added to 14 mL of 4% (v/w) hydrogen chloride in methanol under nitrogen at room temperature. The solution was heated to reflux temperature for 0.5 hours. Upon cooling to room temperature, a precipitate formed which was filtered off and washed with methanol. After vacuum drying (25° C., 15 Pa) 0.72 g (92%) of orange solid was obtained; NMR(DMSO-$d_6$, 250 MHz) 8.10(d,1H, $J_{meta}=2.2$ Hz) 8.04(d,1H, $J_{ortho}=8.3$ Hz), 7.71(dd,1H, $J_{ortho}=8.3, J_{meta}=2.2$ Hz), 6.19(s,1H), 3.92(s,3H).

EXAMPLE 1c 7-chloro-2-hydroxy-1,4-naphthoquinone [Formula IV: $R^1=R^2=R^4=H; R^3=Cl$]

7-chloro-1-tetralone [Formula V; $R^1=R^2=R^4=H; R^3=Cl$] (27.56 g, 0.153 mole) dissolved in 445 mL dry tert-butanol was added over a one hour period to a solution of freshly sublimed potassium tert-butoxide (102.7 g, 0.916 mole) in 1.15L of dry tert-butanol saturated with oxygen at room temperature. Oxygen was bubbled through the solution for two hours after completion of the addition. The mixture was poured into stirred ice cold hydrochloric acid (1.9L, 2N) and extracted with diethyl ether. The ethereal extracts were concentrated in vacuo to give a yellow solid which was triturated with ethyl acetate. The solid was filtered off, washed with water and vacuum dried (25° C., 15 Pa). 10.5 g of yellow solid was then taken up in 0.5 L of hot ethyl acetate and the solution concentrated to 50 mL. Crystallization was initiated by cooling the solution in an ice bath. The solid was filtered off, washed with cold ethyl acetate and hexane. After vacuum drying, (25° C., 15 Pa), 7.10 g (22%) of yellow plates were obtained; mp 215°–216.5° C.

1-tetralones were prepared by the method of Newman and Seshadri, (M. S. Newman and S. Seshadri, J. Org. Chem., 27, 76 (1962). 2-tetralones were prepared by the method of Rosovsky et al, J. Org. Chem., 33, 4288 (1968). 5,7-dibromo-2-tetralone was prepared using 3,5-dibromobenzyl bromide prepared in the following way.

3,5-dibromobenzyl bromide 3,5-dibromotoluene (78.92 g, 0.316 mole) was dissolved in 1.27 L of carbon tetrachloride; to this solution was added N-bromosuccinimide (61.65 g, 0.346 mole) at room temperature. A portion of dibenzoyl peroxide (0.6 g, 0.008 equivalents) was added and the solution heated to reflux temperature for 2.5 hours. The reaction mixture was cooled to room temperature, filtered and the solvent removed in vacuo to yield a solid. The solid was dissolved in 200 mL of warm hexane, filtered and cooled to room temperature. Crystallizations ensued; the crystals were filtered off and washed with cold hexane and air dried to give 45.15 g (44%) of 3,5-dibromobenzyl bromide. $^1$H-NMR(CDCl$_3$); δ 7.6 (1H), 7.47 (2H), 4.36 (2H).

EXAMPLE 1d

7-Chloro-1-tetralone [Formula V: $R^1=R^2=R^4=H; R^3=Cl$]

4-Chlorophenylbutyric acid [Formula VI: $R^1R^2=R^4=H; R^3=Cl$] (26.62 g, 134.0 mM) was added to 150 g of hot polyphosphoric acid (90° C.); the mixture was maintained at 90°–95° C. for 0.33 hours. After cooling to room temperature, the reaction mixture was added to 400 mL of ice cold stirred water. The solution was allowed to warm to room temperature and deposited a precipitate. The solid was filtered off, washed with water and air dried to give 22.3 g (92%) of pale yellow solid. The solid was recrystallized from 50 mL of toluene at −10° C. The crystals were collected and washed with cold toluene and then hexanes to give 18.18 g (75%) of pale yellow crystals; mp 100.3°–101.1° C.

EXAMPLE 1e

4-Chlorophenylbutyric acid [Formula VI: $R^1=R^2=R^3=H; R=Cl$]

4-Chlorobenzoyl propionic acid [Formula VII: $R^1=R^2=R^4=H; R^3=Cl$] (49.94 g, 234.9 mM) was dissolved under nitrogen in 320 mL of triethylene glycol. To the stirred room temperature solution was added potassium hydroxide (44.5 g, 794 mM) followed by 98% hydrazine hydrate (29.0 g, 580.0 mM). The mixture was heated to reflux temperature (142° C.) for 2 hours. Water and hydrazine hydrate were distilled off at atmospheric pressure; the pot temperature rose to 195°–200° C. After 0.5 hours at 195°–200° C., the mixture was cooled to ambient temperature and diluted with 320 mL of water. The aqueous solution was poured into hydrochloric acid (200 mL, 6N) and further diluted with 200 mL of ice water. Upon standing a solid formed which was filtered off, washed with water and vacuum dried (25° C., 15 Pa) to render 43.61 g (93%) of white solid.

EXAMPLES 2–6

A series of 2,5-dihydro-2,5-dioxo-3-hydroxy-1H-benz[b]azepines of formula I was made according to procedures analogous to those presented in Example 1. Table I identifies each such compound by naming each individual substituent $R^i$ ("i" means an integer corresponding to a substituent designation in the formulae) and presents CHN analytical data and melting points for each. Table II also identifies each of the compounds synthesized and presents NMR data.

EXAMPLES 2a–6a

Examples 2a–6a correspond to intermediate methyl ethers of formula II used to make each of the corresponding compounds of Examples 2–6; Table III identifies each of the intermediates and presents 1H-NMR data. Each of the methyl ethers was made according to procedures analogous to those set forth in Example 1a, Procedure A or in Example 1a, Procedure B. The procedure employed for each intermediate is noted in Table III.

EXAMPLES 2b-6b

Examples 2b-6b correspond to the series of 2-methoxy-1,4-naphtoquinones of formula III used to make each of the corresponding intermediate methyl ethers of Examples 2a-6a; Table IV identifies each such compound and presents NMR data.

EXAMPLE 2c

Example 2c (Table V) identifies the 6-chloro-2-hydroxy-1,4-naphthoquinone used to make the corresponding 6-chloro methyl ether of Example 2b. The compound was made by a straightforward application of the method J. M. Lyons and R. H. Thomson, *J. Chem. Soc.*, 1953, 2910-2915. It is noted that Lyons and Thomson reported making a different isomer in their paper, but it is belived that the original assignment they reported was is error.

EXAMPLES 3c-6c

Examples 3c-6c correspond to the series of 2-hydroxy-1,4,-naphthoquinones of formula IV used to make each of the corresponding methyl ethers of Examples 3b-6b; Table V identifies each such compound and presents NMR data.

EXAMPLES 3d-4d

Examples 3d-4d correspond to the series of 1-tetralones used to make the corresponding 2-hydroxy-1,4-naphthoquinones of Examples 3c-4c; Table VI identifies each compound and presents NMR data.

EXAMPLES 5d-6d

Examples 5d-6d correspond to the series of 2-tetralones of formula Va used to make the corresponding 2-hydroxy-1,4-naphthoquinones of Examples 3c-4c; Table VII identifies each compound and presents NMR data.

EXAMPLE 7

The synthetic sequence to make the title compound of Example 7 (compound identified and data set forth in Table I and Table II) proceeded via Scheme I ($R^1=R^3=F$; $R^2=R^4=H$; $R^5=$isopropoxy), and is described following:

5,7-Difluoro-2-methoxy-1,4-naphthoguinone (Compound 20)

A solution of 0.48 g (13.2 mM) of anhydrous hydrogen chloride in 15 mL of methanol was treated with 0.175 g (0.694 mM) of 5,7-difluoro-2-isopropoxy-1,4-naphthoquinone. The mixture was heated to solvent reflux temperature for 0.33 hours, cooled to room temperature and concentrated in vacuo to give 0.13 g of product. $^1$H NMR (dmso-d$_6$): $\delta$ 7.8 (m, 1H), 7.68 (dd, 1H, J$_{H\text{-}ortho}=7.5$ Hz), 6.31 (s, 1H), 3.86(s, 3H).

5,7-difluoro-2-isopropoxy-1,4-naphthoguinone (Compound 18)

A solution of 0.55 g (2.1 mM) of 5,7-difluoro-1,4-dihydroxy-2-isopropoxy-naphthalene in 20 mL of diethyl ether was added over 0.05 hours to a stirred, room temperature solution of 4.05 g (25 mM) of ferric chloride in 46 mL of water and 12 mL of isopropanol. The mixture was stirred for 0.75 hours and then extracted with ethyl acetate. The organic extracts were dried with sodium sulfate, filtered and concentrated to give 0.44 g of tan solid which was recrystalized from 3 mL of warm acetic acid and a few drops of water. After cooling to room temperature, the solid was filtered off, washed with acetonitrile and then water before vacuum drying at room temperature to give 0.057 g of yellow solid. mp 172.0°-173.2°; $^1$H NMR (CDCl$_3$): $\delta=7.68$ (dd, 1H), 7.15 (m, 1H), 6.09 (s, 1H), 4.55 (m, 1H), 1.45(d, 6H).

5,7-difluoro-1,4-dihydroxy-2-isopropoxy-naphthalene (Compound 16)

The THF solution of 2-hydroxy-3-isopropoxy-2-(3,5-difluorophenyl)-3-cyclobutenone, vide infra, was diluted with 40 mL of p-xylene and then concentrated to 16 mL. The p-xylene solution was then diluted to a total volume of 40 mL with additional p-xylene and heated under argon to reflux temperature for 0.42 hours. The solvent was removed in vacuo to yield 0.87 g of amber oil. MS(CI, CH$_4$): m/e=255 (M$^+$+1, base peak).

2-hydroxy-3-isopropoxy-2-(3,5-difluorophenyl)-3-cyclobutenone (Compound 14)

0.753 g (3.9 mM) of 3,5-difluorobromobenzene in 24 mL of dry, distilled THF was cooled under argon to −75° and 2.34 mL of n-butyllithium (1.54M in hexane) added over 0.033 hours. The mixture was kept at −75° to −70° for 0.42 hours and then transferred via cannula to a −75° solution of 0.46 g (3.3 NM) of 3-isopropoxy-3-cyclobutene-1,2-dione in 60 mL of dry, distilled THF over 0.17 hours. The solution was kept at −75° for 0.33 hours at which time 1.4 mL of water was added and stirring continued for 0.17 hours. The reaction solution was poured into a mixture of crushed ice and diethyl ether. The phases were separated and the aqueous phase extracted with additional diethyl ether. The combined organic extracts were dried over sodium sulfate, filtered and concentrated to give a THF solution of the product. MS(CI,CH$_4$): m/e=255 (M$^+$+1, base peak).

3-isopropoxy-3-cyclobutene-1,2-dione (Compound 12)

7.38 g (36.9 mM) of 2,3-diisopropoxy-4-hydroxy-2-cyclobutenone in 116 mL of methylene chloride was stirred with 2 mL of concentrated hydrochloric acid at room temperature for 1 hour. The solution was neutralized and dried over potassium carbonate and sodium sulfate, filtered and concentrated in vacuo to give 5.14 g of red oil. The oil was flash chromatographed on SiO$_2$ (7.5 cm diameter × 10 cm column) using diethyl ether - hexane (1:1) as eluant. Concentration of the major fraction gave 4.14 g (80%) of yellow oil. $^1$H NMR (CDCl$_3$): $\delta=8.48$ (s,1H), 5.02 (m, 1H), 1.49 (d, 6H); MS(CI, CH$_4$): m/e=141 (M$^+$+1), 99 (base peak).

2,3-diisopropoxy-4-hydroxy-2-cyclobutenone (Compound 13)

A solution of 10.02 g (50.55 mM) of 3,4-diisopropoxy-3-cyclobutene-1,2-dione in 100 mL of dry, distilled THF was cooled to −10° and was treated over 0.66 hours with a solution of 16.0 g (63.1 mM) of lithium tri-(tert-butoxy)aluminum hydride in 63 mL of dry, distilled THF, while maintaining a −5° to −10° internal temperature. The temperature was maintained at −5° for an additional 0.5 hours. To a stirred, saturated aqueous solution of potassium sodium tartrate and 50 mL of diethyl ether was added the reaction mixture. The organic layer was separated and the aqueous phase extracted with diethyl ether. The combined extracts were dried over sodium sulfate, filtered and concentrated in vacuo to give 8.12 g of yellow oil. The oil was flash chromatographed on $SiO_2$ (7 cm diameter × 8.5 cm column) using diethyl ether/hexane (1:1) as eluant. Concentration of the major fraction gave 7.38 g (73%) of colorless oil. $^1$H NMR ($CDCl_3$): $\delta$=4.9 (m, 3H), 2.65 (bs, 1H), 1.42 (d, 6H), 1.30 (m, 6H); MS(CI, $CH_4$): m/e=201 ($M^+$+1),159 (base peak).

EXAMPLE 8

The following illustrate representative pharmaceutical dosage forms containing a compound of formula I or of formula II, for example as illustrated in any of the previous Examples, (hereafter referred to as "Compound X"), for therapeutic or prophylactic use in humans:

|  | mg/tablet |
|---|---|
| (a) Tablet |  |
| Compound X | 50.0 |
| Mannitol, USP | 223.75 |
| Croscarmellose sodium | 6.0 |
| Maize starch | 15.0 |
| Hydroxypropylmethylcellulose (HPMC), USP | 2.25 |
| Magnesium stearate | 3.0 |
| (b) Capsule |  |
| Compound X | 10.0 |
| Mannitol, USP | 488.5 |
| Croscarmellose sodium | 15.0 |
| Magnesium stearate | 1.5 |

The above formulations may be obtained by conventional procedures well known in the pharmaceutical art. The tablets may be enteric coated by conventional means, for example to provide a coating of cellulose acetate phthalate.

EXAMPLE 9

The following is a description of an injectable formulation made with the compound of Example 1.

A series of aqueous solutions of varying concentrations of the compound of Example 1 (the "Compound") were made. An aqueous solution formulation suitable for intravenous administration containing 3.5 mg/mL of the Compound was made by (1) dissolving Meglumine (N-methylglucamine) in water in an amount sufficient to make a 19.5 mg/mL solution; (2) dissolving the Compound in the solution in an amount sufficient to achieve the desired concentration of Compound of 3.5 mg/ml; and (3) adding sodium chloride or dextrose in an amount sufficient to achieve isotonicity. Concentrations of drug less than 3.5 mg/mL were also made. The formulations were manufactured using typical manufacturing procedures for parenteral products, for example by using sonication as required to help effect dissolution of the Compound.

TABLE I

Analytical Data and Melting Points for
2,5-dihydro-2,5-dioxo-3-hydroxy-1H-benz[b]azepines (Formula I)

| Ex. No. | $R^i$= | mp | Formula |  | C | H | N |
|---|---|---|---|---|---|---|---|
| 2 | $R^1$=$R^3$=$R^4$=H; $R^2$=Cl | 278 | $C_{10}H_6ClNO_3$ | cal | 53.71 | 2.70 | 6.26 |
|  |  |  |  | fnd | 53.51 | 2.93 | 6.57 |
| 3 | $R^1$=$R^2$=$R^4$=H; $R^3$=Br | 182–186 | $C_{10}H_6BrNO_3$ | cal | 46.84 | 2.86 | 4.97 |
|  |  |  |  | fnd | 47.21 | 2.65 | 5.31 |
| 4 | $R^1$=$R^2$=$R^4$=H; $R^3$=F | 201–203 | $C_{10}H_6FNO_3$ | cal | 57.98 | 2.92 | 6.76 |
|  |  |  |  | fnd | 57.62 | 2.89 | 6.83 |
| 5 | $R^1$=$R^3$=Cl; $R^2$=$R^4$=H | 194–197 | $C_{10}H_5Cl_2NO_3$ | cal | 46.54 | 1.95 | 5.43 |
|  |  |  |  | fnd | 46.25 | 1.95 | 5.42 |
| 6 | $R^1$=$R^3$=Br; $R^2$=$R^4$=H | 275–276 (dec) | $C_{10}H_5Br_2NO_3$ | cal | 34.62 | 1.45 | 4.04 |
|  |  |  |  | fnd | 34.75 | 1.26 | 4.16 |
| 7 | $R^1$=$R^3$=F; $R^2$=$R^4$=H | 259–260 | $C_{10}H_5F_2NO_3$ |  |  |  |  |

TABLE II $^1$H-NMR for 2,5-dihydro-2,5-dioxo-3-hydroxy-1H-benz[b]azepines in dmso-$d_6$ (Formula I)

| Ex. No. | $R^i$= |  |
|---|---|---|
| 2 | $R^1$=$R^3$=$R^4$=H; $R^2$=Cl | 11.70(s, 1H, NH), 10.77(brs, 1H, OH)7.98(d, 1H, $J_{meta}$=2.6Hz), 7.72(dd, 1H, $J_{ortho}$=8.8Hz, $J_{meta}$=2.6Hz), n7.5(d, 1H, $J_{ortho}$=8.8Hz), 6.44(s, 1H). |
| 3 | $R^1$=$R^2$=$R^4$=H; $R^3$=Br | 11.64(s, 1H, NH), 10.8(brs, 1H, OH), 7.95(d, 1H, $J_{ortho}$=8.67), 7.71(d, 1H, $J_{meta}$=1.65Hz)7.43(dd, 1H, $J_{ortho}$=8.67Hz, $J_{meta}$=1.65Hz), 6.43(s, 1H) |
| 4 | $R^1$=$R^2$=$R^4$=H; $R^3$=F | 11.69(s, 1H, NH), 10.82(brs, 1H, OH), 8.11(dd, 1H, 7.27 (dd, 1H), 7.14(m, 1H), 6.44(s, 1H) |
| 5 | $R^1$=$R^3$=Cl; $R^2$=$R^4$=H | 11.43(s, 1H, NH), 10.84(brs, 1H, OH), 7.544(d, 1H, $J_{meta}$=1.87Hz), 7.42(d, 1H, $J_{meta}$=1.87Hz), 6.37(s, 1H) |
| 6 | $R^1$=$R^3$=Br; R2=$R^4$=H | 11.37(s, 1H, NH), 10.83(s, 1H, OH), 7.79(d, 1H, $J_{meta}$=1.1Hz), 7.58(d, 1H, $J_{meta}$=1.1Hz), 6.35(s, 1H) |
| 7 | $R^1$=$R^3$=F; $R^2$=$R^4$=H | 11.53(s, 1H, NH), 10.8(brs, 1H, OH), 7.15(t, 1H), 7.02(d, 1H, $J_{HFortho}$=10.6Hz), 6.28(s, 1H) |

TABLE III $^1$H-NMR for 2,5-dihydro-2,5-dioxo-3-methoxy-1H-benz[b]azepine in dmso-$d_6$ (Formula II, $R^5$=$CH_3$)

| Ex. No. | $R^i$= | Method of Prep |  |
|---|---|---|---|
| 2a | $R^1$=$R^3$=$R^4$=H; $R^2$=Cl | A | 11.47(s, 1H, NH)7.88(d, 1H, $J_{meta}$=2.6Hz), 7.69(dd, H, $J_{ortho}$=8.8Hz, $J_{meta}$=2.6Hz), 7.44(d, 1H, $J_{ortho}$=8.8Hz), 6.38(s, 1H), 3.82(s, 3H). |

TABLE III-continued $^1$H-NMR for 2,5-dihydro-2,5-dioxo-3-methoxy-1H-benz[b]azepine in dmso-$d_6$ (Formula II, $R^5$=CH$_3$)

| Ex. No. | $R^i$= | Method of Prep | |
|---|---|---|---|
| 3a | $R^1=R^2=R^4$=H; $R^3$=Br | B | 11.09(s, 1H, N$\underline{H}$)7.78(d, 1H, J$_{ortho}$=8.53Hz), 7.50 (d, 1H, J$_{meta}$=1.65Hz), 7.24(dd, 1H, J$_{ortho}$=8.53Hz, J$_{meta}$=1.65Hz), 6.24(s, 1H)3.76(s, 3H). |
| 4a | $R^1=R^2=R^4$=H; $R^3$=F | B | 8.06(dd, 1H), 7.23(dd, 1H), 7.11(m, 1H)6.36(s, 1H), 3.81(s, 3H). |
| 5a | $R^1=R^3$=Cl; $R^2=R^4$=H | B | 11.28(s, 1H, N$\underline{H}$), 7.54(s, 1H), 7.36(s, 1H), 6.44(s, 1H), 3.74(s, 3H). |
| 6a | $R^1=R^3$=Br; $R^2=R^4$=H | B | 11.22(s, 1H, N$\underline{H}$), 7.79(d, 1H, J$_{meta}$=1.7Hz)7.54(d, 1H, J$_{meta}$=1.7Hz), 6.43(s, 1H), 3.26(s, 3H). |
| 7a | $R^1=R^3$=F; $R^2=R^4$=H | B | 11.39(brs, 1H, N$\underline{H}$), 7.18(m, 1H), 6.19(dd, 1H, J$_{HFortho}$=10.5Hz, J$_{meta}$=2.2Hz), 6.35(s, 1H), 3.76(s, 1H). |

TABLE IV $^1$H-NMR for 2-methoxy-1,4-naphthoquinone in dmso-$d_6$ (Formula III, $R^5$=CH$_3$)

| Ex. No. | $R^i$= | |
|---|---|---|
| 2b | $R^1=R^3=R^4$=H; $R^2$=Cl | 8.08(d, 1H, J$_{ortho}$=8.0Hz), 8.06(d, 1H, J$_{meta}$=2.1Hz)7.67 (dd, 1H, J$_{ortho}$=8.0Hz, J$_{meta}$=2.1Hz), 6.19(s, 1H), 3.92(s, 3H). |
| 3b | $R^1=R^2=R^4$=H; $R^3$=Br | 8.10(d, 1H, J$_{meta}$=1.92Hz), 8.06(dd, 1H, J$_{ortho}$=8.26Hz, J$_{meta}$=1.92Hz), 7.91(d, 1H, J$_{ortho}$=8.26Hz), 6.39(s, 1H), 3.9 (s, 3H) |
| 4b | $R^1=R^2=R^4$=H; $R^3$=F | 8.04(m, 1H), 7.72(m, 2H), 6.37(s, 1H), 3.87(s, 3H) |
| 5b | $R^1=R^3$=Cl; $R^2=R^4$=H | 8.10(d, 1H, J$_{meta}$=2.2Hz), 7.97(d, 1H, J$_{meta}$=2.2Hz), 6.37(s, 1H), 3.86(s, 3H) |
| 6b | $R^1=R^3$=Br; $R^2=R^4$=H | 8.30(d, 1H, J$_{meta}$=1.9Hz), 8.16(d, 1H, J$_{meta}$=1.9Hz), 6.20(s, 1H), 3.90(s, 3H) |

TABLE V $^1$H-NMR for 2hydroxy-1,4-naphthoquinone in dmso-$d_6$ (Formula IV)

| Ex. No. | $R^i$= | |
|---|---|---|
| 2c | $R^1=R^3=R^4$=H; $R^2$=Cl | 8.08 (d, 1H, J$_{meta}$=2.3Hz), 8.07(d, 1H, J$_{ortho}$=7.9Hz), 7.68 (dd, 1H, J$_{ortho}$=7.9Hz, J$_{meta}$=2.3Hz), 7.37(brs, 1H, O$\underline{H}$), 6.38 (s, 1H). |
| 3c* | $R^1=R^2=R^4$=H; $R^3$=Br | 8.08(d, 1H, J$_{meta}$=1.89Hz), 8.02(dd, 1H, J$_{ortho}$=8.25Hz, J$_{meta}$=1.89Hz), 7.87(d, 1H, J$_{ortho}$=8.7), 6.22(s, 1H) |
| 4c | $R^1=R^2=R^4$=H; $R^3$=F | 8.0(m, 1H), 7.68(m, 2H), 6.17(s, 1H) |
| 5c | $R^1=R^3$=Cl; $R^2=R^4$=H | 8.09(d, 1H, J$_{meta}$=2.2Hz), 7.8(d, 1H, J$_{meta}$=2.2Hz), 7.07(s, 1H, O$\underline{H}$), 6.38(s, 1H) |
| 6c | $R^1=R^3$=Br; $R^2=R^4$=H | 8.29(d, 1H, J$_{meta}$=2.0Hz), 8.21(d, 1H, J$_{meta}$=2.0Hz), 7.1(s, 1H, O$\underline{H}$), 6.4(s, 1H) |

*TFA-$d_1$ added to dmso-$d_6$

TABLE VI $^1$H-NMR for 1-tetralones in CDCl$_3$ (Formula V)

| Ex. No. | $R^i$= | |
|---|---|---|
| 3d | $R^1=R^2=R^4$=H; $R^3$Br | 7.92(d, 1H, J$_{meta}$=2.26Hz), 7.73(dd, 1H, J$_{ortho}$=8.16Hz, J$_{meta}$=2.26Hz), 7.34(d, 1H, J$_{ortho}$=8.16Hz), 2.91(t, 2H, J$_{H34}$=6.01Hz), 2.62(t, 2H, 6.16Hz), 2.04(m, 2H) |
| 4d | $R^1=R^2=R^4$=H; $R^3$=F | 7.54(m, 1H), 7.42(m, 2H), 2.93(t, 2H, J$_{H34}$=5.98Hz), 2.61 (t, 2H, J$_{H23}$=6.19Hz), 2.04(m, 2H) |

TABLE VII $^1$H-NMR for 2-tetralones in CDCl$_3$ (Formula Va)

| Ex. No. | $R^i$= | |
|---|---|---|
| 5d | $R^1=R^3$=Cl; $R^4$H | 7.32(d, 1H, J$_{meta}$=2.0Hz), 7.05(d, 2H, J$_{meta}$=2.0Hz), 3.57(s, 2H), 3.91(t, 2H, J$_{H34}$=6.8Hz), 2.56(t, 2H, J$_{H34}$=6.8Hz) |
| 6d | $R^1=R^3$=Br; $R^2=R^4$=H | 7.65(d, 1H, J$_{meta}$=1.9Hz), 7.24(d, 1H, J=1.9Hz), 3.57(s, 1H), 3.81(t, 2H, J$_{H34}$=6.7Hz), 2.56(t, 2H, J$_{H34}$=6.7Hz) |

CHEMICAL FORMULAE

17
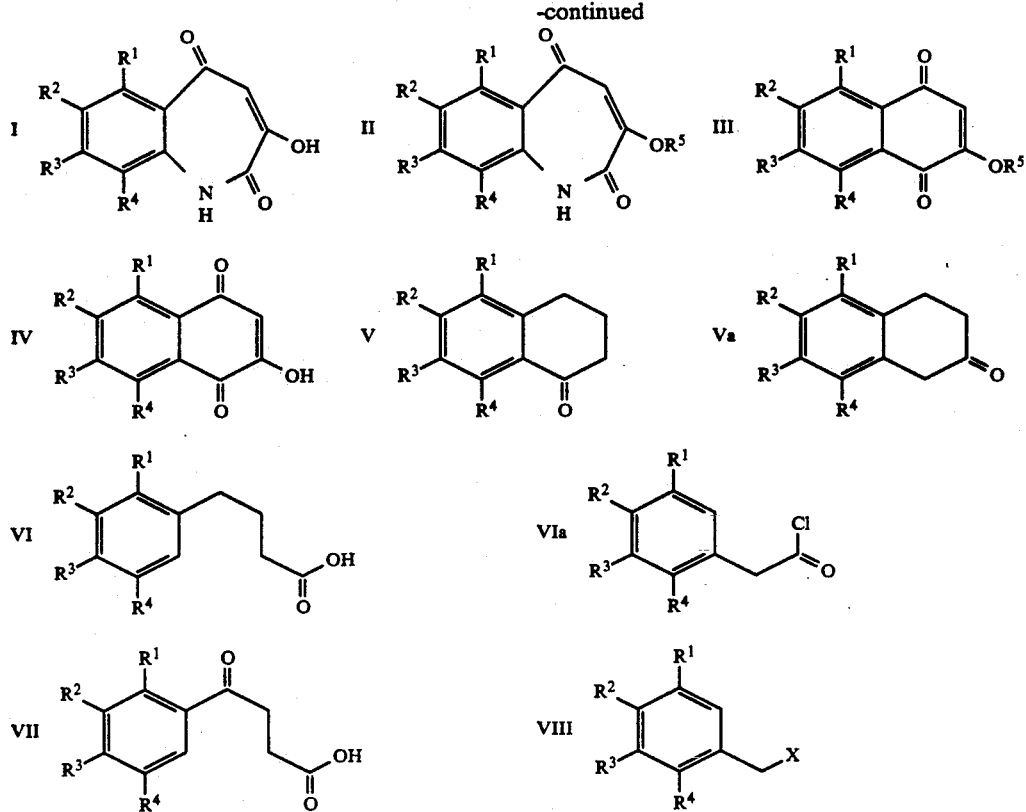
SCHEME I
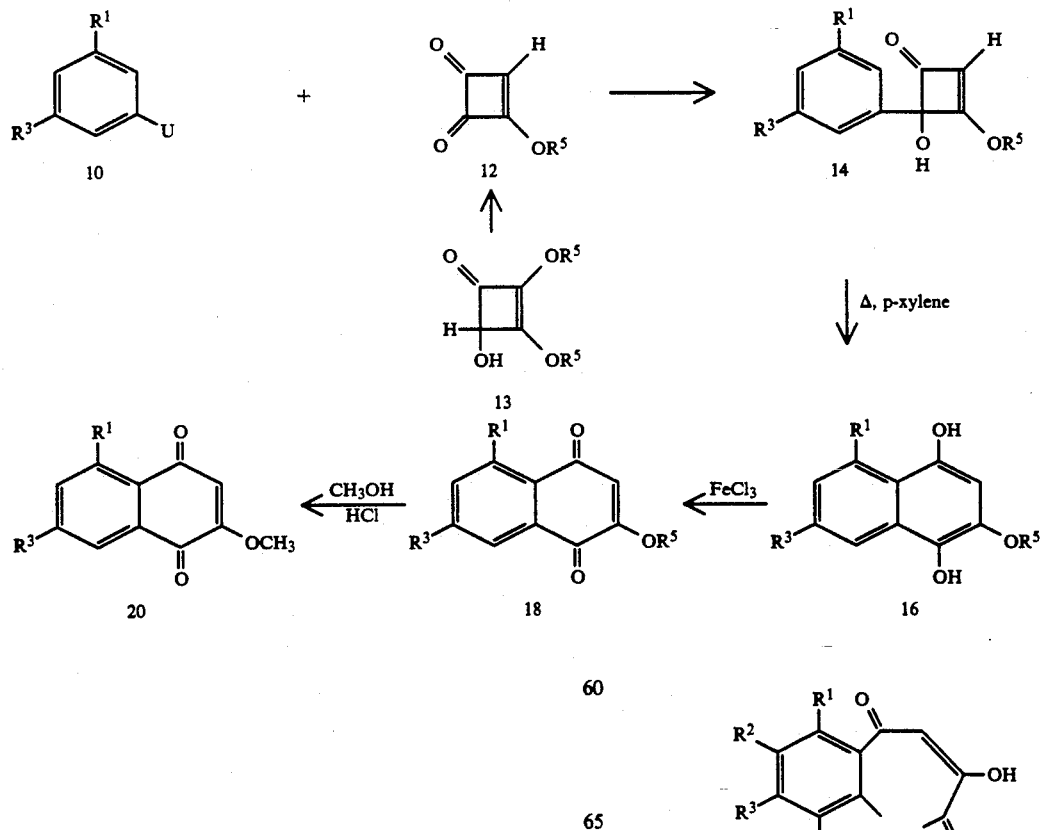
What is claimed is:
1. A compound of formula I or of formula II, formulae set out hereinbelow, wherein:
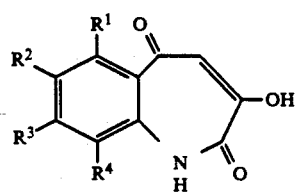
or

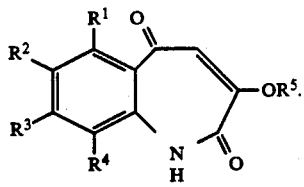

$R^1$, $R^2$, $R^3$ and $R^4$ are independently selected from:
hydrogen,
(1–3C)perfluoroalkyl,
halo, nitro and cyano;
$R^5$ is a (1–5C)alkyl group;
provided that $R^2$ and $R^3$ are not both (independently) selected from the group consisting of hydrogen and halogen when $R^1$ and $R^4$ are hydrogen;
and pharmaceutically acceptable salts of compounds of formula I.

2. A compound as defined in claim 1, wherein:
$R^1$, $R^2$, $R^3$, and $R^4$ are independently selected from hydrogen, trifluoromethyl, pentafluoroethyl, heptafluoropropyl, and halo; and
$R^5$ is selected from methyl, ethyl, propyl, isopropyl, butyl, isobutyl, pentyl, isopentyl, and neopentyl.

3. A compound as defined in claim 2, wherein:
$R^1$, $R^2$, $R^3$, and $R^4$ are independently selected from hydrogen, trifluoromethyl and halo;
$R^5$ is selected from methyl, ethyl, and propyl.

4. A compound as defined in claim 3, wherein:
$R^1$, $R^2$, $R^3$, and $R^4$ are independently selected from hydrogen, fluoro, chloro, and bromo; and
$R^5$ is selected from methyl and ethyl.

5. A compound as defined in claim 1, selected from:
6,8-dichloro-2,5-dihydro-2,5-dioxo-3-hydroxy-1H-benz[b]azepine;
6,8-dibromo-2,5-dihydro-2,5-dioxo-3-hydroxy-1H-benz[b]azepine;
6,8-difluoro-2,5-dihydro-2,5-dioxo-3-hydroxy-1H-benz[b]azepine;
and (1–5C)alkyl enol ethers thereof.

6. A compound which is selected from:
8-chloro-2,5-dihydro-2,5-dioxo-3-hydroxy-1H-benz[b]azepine;
8-bromo-2,5-dihydro-2,5-dioxo-3-hydroxy-1H-benz[b]azepine; and
8-fluoro-2,5-dihydro-2,5-dioxo-3-hydroxy-1H-benz[b]azepine;
pharmaceutically-acceptable salts thereof, and (1–5C)alkyl enol ethers thereof.

7. A compound according to claim 6, wherein the compound is 8-chloro-2,5-dihydro-2,5-dioxo-3-hydroxy-1H-benz[b]azepine.

* * * * *